US006387416B1

(12) United States Patent
Newmark et al.

(10) Patent No.: US 6,387,416 B1
(45) Date of Patent: May 14, 2002

(54) ANTI-INFLAMMATORY HERBAL COMPOSITION AND METHOD OF USE

(76) Inventors: Thomas Newmark, 704 Cordell Ct., St. Louis, MO (US) 63132; Paul Schulick, 222 Kipling Rd., Brattleboro, VT (US) 05301

( * ) Notice: Subject to any disclaimer, the term of this patent is extended or adjusted under 35 U.S.C. 154(b) by 0 days.

(21) Appl. No.: 09/825,838

(22) Filed: Apr. 5, 2001

(51) Int. Cl.$^7$ .................. A01N 65/00; A61K 35/78; A61K 39/385
(52) U.S. Cl. ................ 424/725; 424/756; 424/729; 424/777; 424/745
(58) Field of Search ................ 424/725, 195.1, 424/729, 756, 777, 745

(56) References Cited

U.S. PATENT DOCUMENTS 5,494,668 A    2/1996   Patwardhan
5,683,698 A   11/1997   Chavali et al.
5,854,291 A   12/1998   Laughlin et al.
5,910,307 A    6/1999   Kwak et al.
5,916,565 A    6/1999   Rose et al.

*Primary Examiner*—Christopher R. Tate
*Assistant Examiner*—Patricia A Patten
(74) *Attorney, Agent, or Firm*—Patton Boggs LLP

(57) ABSTRACT

An orally or topically administered composition capable of reducing inflammation in animals, preferably humans, suffering from inflammation, contains a therapeutically effective amount of a post-supercritical carbon dioxide alcoholic extract of ginger; therapeutically effective amounts of supercritical carbon dioxide extracts of rosemary, turmeric, oregano and ginger (preferably certified organic ginger); and therapeutically effective amounts of hydroalcoholic extracts of holy basil, turmeric, scutellariae baicalensis, rosemary, green tea, huzhang, Chinese goldthread, and barberry. The composition is preferably orally administered on a daily basis for at least about 4 weeks.

43 Claims, No Drawings

ANTI-INFLAMMATORY HERBAL COMPOSITION AND METHOD OF USE

BACKGROUND OF THE INVENTION

This invention relates to herbal compositions. More particularly, this invention relates to an herbal composition capable of reducing inflammation in bones and joints in animals, particularly humans. The present invention further relates to methods of using such herbal composition to reduce inflammation in bones and joints in animals, particularly humans.

Arthritic disorders, including rheumatism, osteoarthritis, dysplasia, lupus, bursitis, and gout, are all characterized by inflammation and pain in bones, joints, muscles, and related connective tissues. Most of the forms are progressive. Bone and joint inflammation is a scourge of both animals and humans. Those who suffer from inflammation experience pain and discomfort and may, in advanced cases, lose the effective use of inflamed joints. Thus, the goal of therapeutic methods for treating bone or joint inflammation is the relief of pain and discomfort and the restoration of use of inflamed joints.

Natural ingredients, e.g., herbs, have been used to treat bone and joint inflammation, especially in eastern countries, and, increasingly, in western countries. Compositions composed of natural ingredients and said to be useful in reducing inflammation are disclosed, e.g., in U.S. Pat. Nos. 5,494,668; 5,683,698; 5,916,565; 5,854,291; and 5,910,307.

U.S. Pat. No. 5,494,668 (Patwardhan) discloses a method of treating degenerative musculoskeletal diseases such as rheumatoid arthritis and osteoarthritis in an animal, typically a human, involving administering (typically enterally) to the animal beneficiated extracts of the ashwagandha, sallai Guggul, turmeric, and ginger plants, in a predetermined proportion relative to each other with or without other biologically active inorganic ingredients.

U.S. Pat. No. 5,683,698 (Chavali et al.) discloses an orally administered herbal formulation for reducing or alleviating symptoms associated with rheumatoid arthritis, osteoarthritis, and reactive arthritis and for reducing the production of pro-inflammatory cytokines, wherein the formulation contains herbal extracts taken from Alpinia, Smilax, Tinospora, Tribulus, Withania, and Zingiber plants.

U.S. Pat. No. 5,916,565 (Rose et al.) discloses an orally administered composition for prophylaxis and therapy of joint and connective tissue disorders in vertebrates, wherein the composition contains metabolic precursors, herbal phytochemicals, and palatability agents. Specific herbal phytochemicals disclosed include cayenne, ginger, turmeric, yucca, Devil's claw, nettle leaf, Black Cohosh, alfalfa and celery seeds.

U.S. Pat. No. 5,854,291 (Laughlin, et al.) discloses a topically-applied pain reliever composition for treating such discomforts as arthritis pain, the composition being composed of capsaicin and, optionally, a plant extract selected from the group consisting of nettle extract, yarrow extract, coltsfoot extract, birch extract, rosemary extract, horsetail extract, ginger extract, chamomile extract, comfrey extract, lavender extract, and bergamot extract.

U.S. Pat. No. 5,910,307 (Kwak, et al.) discloses a combined medicinal plant composition for alleviating acute/chronic inflammation, composed of Clematis Radix, Trichosanthes root, and Prunella Herba (which contains oleanolic acid ursolic acid) in a certain ratio.

Certain enzymes appear to play a role in causing inflammation. One of the features of inflammation is increased oxygenation of arachidonic acid which is metabolized by two enzymic pathways—the cyclooxygenase (CO) and the 5-lipoxygenase (5-LO) pathways—leading to the production of prostaglandins and leukotrienes, respectively. Prostaglandins and leukotrienes are mediators of inflammation. Therapies designed to inhibit cyclooxygenase and/or lipoxygenase activity are therefore of great interest.

There are two forms of the cyclooxygenase enzyme: cyclooxygenase-1 (COX-1) and cyclooxygenase-2 (COX-2). The latter form, i.e., COX-2, appears to play a key role in inflammatory processes. Recent scientific studies suggest that inhibiting the COX-2 enzyme may be an effective way to reduce inflammation without the side effects associated with irreversible COX-1 inhibition. In addition, recent scientific studies also suggest that COX-2 inhibition may serve an important function in promoting normal cell growth in the colon, pancreas, breast tissue and other organ systems.

Drugs are being developed which are intended to selectively inhibit COX-2 with minimal effect on COX-1. However, despite the emphasis on COX-2 inhibition, these drugs appear to have serious side effects, e.g., a breakdown in digestive protective mucus and prevention of normal healing processes. For example, non-steroidal anti-inflammatory drugs (NSAIDS) can have a variety of toxic side effects such as, e.g., gastric erosion and adverse effects on kidneys and liver, and may inadequately regulate the cellular immune functions and secretions of various cytokines.

Several herbs have been found to inhibit the COX-2 enzyme.

For example, holy basil has been found to possess significant anti-inflammatory properties and is capable of blocking both the cyclooxygenase and lipoxygenase pathways of arachidonate metabolism. Ursolic acid and oleanolic acid (less active), the marker constituents of holy basil, have been found to a significant COX-2 inhibitory effect.

Shogaol, a pungent component of ginger, has been found to inhibit cyclooxygenase. Eugenol, another constituent of ginger, has also been found to be a 5-lipoxygenase inhibitor and to possess potent anti-inflammatory and/or anti-rheumatic properties.

Scutellaria baicalensis also has been found to inhibit the COX-2 enzyme.

According to the USDA database, green tea contains six constituents having cyclooxygenase-inhibitor activity. According to the Napralert database, green tea contains fifty one constituents having anti-inflammatory activity. The polyphonies in green tea were found to cause a marked reduction in cyclooxygenase-2. Flavan-3-ol derivatives (+)-catechin, also present in green tea, have been reported to be COX-1 and COX-2 inhibitors. In addition, salicylic acid, another constituent of green tea, also has been found to be a COX-2 inhibitor.

Berberine, found in barberry and Chinese goldthread, has been found to inhibit COX-2 without inhibiting COX-1 activity.

Inflammation is also mediated by oxygen-derived free radicals. Free radicals degrade hyaluronic acid, modify collagen and perhaps proteoglycan structure and/or synthesis, alter and interact with immunoglobulins, activate degradative enzymes and inactivate their inhibitors, and possibly participate in chemotaxis. It is desirable to scavenge and detoxify free radicals before they reach the affected area.

Herbs which can scavenge free radicals include, e.g., holy basil, turmeric, huzhang, oregano, and scutellaria baicalensis.

Although herbs having anti-inflammatory properties are known, it is continually desirable to provide herbal compositions which have improved anti-inflammatory properties.

Accordingly, a primary object of this invention is to provide an orally administered herbal composition capable of effectively reducing bone and joint inflammation in animals, particularly humans.

A further object of this invention is to provide the herbal composition set forth in the preceding object, wherein the composition reduces said inflammation by inhibiting COX-2.

Another object of this invention is to provide the herbal composition set forth in the preceding objects, wherein the composition is capable of reducing inflammation while avoiding the side effects associated with traditional drug therapy.

A further object of this invention is to provide the herbal composition set forth in the preceding objects, wherein the composition also has antioxidant properties.

A still further object of this invention is to provide the herbal composition described in the preceding objects, wherein the composition is composed of herbal extracts that are prepared without chemical solvents.

Yet another object of this invention is to provide a method of reducing inflammation in animals (particularly humans) using an herbal composition having the properties set forth in the preceding objects.

These objects and others are achieved in the present invention.

SUMMARY OF THE INVENTION

The present invention is based on the discovery that a combination of certain herbs properly extracted and blended in appropriate proportions can provide improved anti-inflammatory benefits.

Accordingly, one aspect of the present invention is directed to an orally or topically administered herbal composition capable of reducing inflammation in animals, preferably humans, afflicted with inflammation, the composition being composed of a therapeutically effective amount of a post-supercritical carbon dioxide alcoholic extract of ginger; therapeutically effective amounts of supercritical carbon dioxide extracts of rosemary, turmeric, oregano and ginger (preferably certified organic ginger); and therapeutically effective amounts of hydroalcoholic extracts of holy basil, turmeric, scutellariae baicalensis, rosemary, green tea, huzhang (*Polygonumn cuspidatum*), Chinese goldthread, and barberry.

A second aspect of the present invention is directed to a method for reducing inflammation in animals, preferably humans, suffering from inflammation, the method involving the steps of:

(1) providing the composition of this invention; and
(2) orally or topically administering the composition to the animal in an
   amount and for a time period effective to reduce inflammation in the animal.

The composition of this invention reduces inflammation by inhibiting COX-2. As a result, the composition not only reduces inflammation but also promotes healthy joint function and normal cell growth.

In addition, the composition of this invention is capable of scavenging toxic active oxygen species, thereby providing antioxidant benefits.

Another benefit provided by the composition of this invention is that it can be prepared without the use of chemical solvents. This feature is achieved by using a supercritical solvent-free extraction process to obtain the extracts. Such extraction process allows for the highest potency of active compounds in the extracts, as much as 250 times the potency of the original fresh plant material.

DETAILED DESCRIPTION OF THE INVENTION

As stated above, the present invention provides an orally or topically administered herbal composition and a method of using the composition to reduce inflammation in animals, preferably humans, suffering from inflammation.

The composition of this invention is composed of: a post-supercritical carbon dioxide alcoholic extract of ginger; supercritical carbon dioxide extracts of rosemary, turmeric, oregano and ginger (preferably certified organic ginger); and hydroalcoholic extracts of holy basil, turmeric, scutellariae baicalensis, rosemary, green tea, huzhang, Chinese goldthread and barberry.

The composition of this invention will contain "therapeutically effective amounts" of the herbal extracts recited above. As used herein with respect to each of the herbal extracts used in the composition of this invention, the term "therapeutically effective amount" refers to that amount of the extract which will contribute to the inflammation-reducing ability of the composition.

Preferably, the composition of this invention contains:

(A) from about 4.5% to about 7.5%, more preferably from about 5.5% to about 6.5%, by weight of a post-supercritical carbon dioxide alcoholic extract of ginger, (B) from about 5.5% to about 8.5%, more preferably from about 6% to about 8%, by weight of a supercritical carbon dioxide extract of ginger, (C) from about 1.0% to about 1.5%, more preferably from about 1.2% to about 1.4%, by weight of a supercritical carbon dioxide extract of turmeric;

(D) from about 10.0% to about 16.0%, more preferably from about 11.5% to about 14.5%, by weight of a supercritical carbon dioxide extract of rosemary, (E) from about 4.0% to about 6.0%, more preferably from about 4.5% to about 5.5%, by weight of a supercritical carbon dioxide extract of oregano;

(F) from about 10.0% to about 16.0%, more preferably from about 11.5% to about 14.5%, by weight of a hydroalcoholic extract of turmeric;

(G) from about 5.5% to about 8.0%, more preferably from about 6.0% to about 7.0%, by weight of a hydroalcoholic extract of rosemary, (H) from about 10.0% to about 16.0%, more preferably from about 11.5% to about 14.5%, by weight of a hydroalcoholic extract of holy basil;

(I) from about 10.0% to about 16.0%, more preferably from about 11.5% to about 14.5%, by weight of a hydroalcoholic extract of green tea;

(J) from about 8.0% to about 12.0%, more preferably from about 9.0% to about 11.0%, by weight of a hydroalcoholic extract of huzhang;

(K) from about 4.0% to about 6.0%, more preferably from about 4.5% to about 5.5%, by weight of a hydroalcoholic extract of Chinese goldthread;

(L) from about 4.0% to about 6.0%, more preferably from about 4.5% to about 5.5%, by weight of a hydroalcoholic extract of barberry; and (M) from about 2.0% to about 3.0%, more preferably from about 2.25% to about 2.75%, by weight of a hydroalcoholic extract of scutellariae baicalensis.

The post-supercritical carbon dioxide alcoholic extract of ginger used in the present invention is preferably prepared as follows. The ginger rhizome, which is preferably cryogenically ground to preserve heat sensitive components, is subjected to supercritical carbon dioxide extraction to obtain: (i) an oil extract (referred to herein as "the supercritical carbon dioxide extract" of ginger) containing delicate lipophilic (oil-soluble/non-polar) components, and (ii) an oil-free residue. The oil-free residue is then extracted in a water/alcohol (preferably water/ethanol) mixture (composed of 60–80 parts alcohol and 40–20 parts water). The alcohol/water liquid is then evaporated off, leaving a powdered extract residue, referred to herein as "the post-supercritical carbon dioxide hydroalcoholic extract" of ginger.

The composition of this invention will preferably contain the supercritical carbon dioxide extract and the post-supercritical carbon dioxide hydroalcoholic extract of ginger at a weight ratio of preferably from about 0.9 to about 1.4 parts, more preferably from about 1.1 to about 1.3 parts, most preferably about 1.17 parts, of supercritical carbon dioxide extract per 1 part post-supercritical carbon dioxide hydroalcoholic extract.

The supercritical carbon dioxide extracts of ginger, rosemary, turmeric and oregano used in the present invention can be prepared according to known supercritical carbon dioxide extraction methods, such as disclosed, e.g., in E. Stahl, K. W. Quirin, D. Gerard, Dense Gases for Extraction and Refining, *Springer Verlag* 4 1988, which is hereby incorporated by reference herein.

The hydroalcoholic extracts of rosemary, turmeric, holy basil, green tea, huzhang, Chinese goldthread, barberry and scutellariae baicalensis used in the present invention can be prepared according to conventional hydroalcoholic extraction techniques. For example, the hydroalcoholic extracts can be prepared by extracting the plant portion in a water/alcohol (preferably water/ethanol) mixture (preferably composed of 60–80 parts alcohol and 40–20 parts water), and then evaporating off the water/alcohol liquid, leaving a powdered extract residue (referred to herein as "the hydroalcoholic extract").

In the composition of this invention, the hydroalcoholic extract of turmeric and the supercritical carbon dioxide extract of turmeric will preferably be present at a weight ratio of preferably from about 8 to about 12 parts, more preferably from about 9 parts to about 11 parts, most preferably about 10 parts, of hydroalcoholic extract per 1 part of supercritical carbon dioxide extract.

The composition of this invention will preferably contain the supercritical carbon dioxide extract of rosemary and the hydroalcoholic extract of rosemary at a weight ratio of preferably from about 1.6 to about 2.4 parts, more preferably from about 1.8 to about 2.2 parts, most preferably about 2.0 parts, of supercritical carbon dioxide extract per 1 part of hydroalcoholic extract.

The post-supercritical carbon dioxide hydroalcoholic extract of ginger used in the present invention will preferably contain from about 2.4% to about 3.6%, more preferably from about 2.7% to about 3.3%, most preferably about 3.0%, by weight of pungent compounds (e.g., shogaol).

The supercritical carbon dioxide extract of ginger used in the present invention will contain preferably from about 24% to about 36%, more preferably from about 27% to about 33%, most preferably about 30%, by weight of pungent compounds (e.g., shogaol) and preferably from about 6.4% to about 9.6%, more preferably from about 7.2% to about 8.8%, most preferably about 8%, by weight of zingiberene.

The supercritical carbon dioxide extract of turmeric used in the present invention will contain preferably from about 36% to about 54%, more preferably from about 40.5% to about 49.5%, most preferably about 45%, by weight of turmerones.

The supercritical carbon dioxide extract of rosemary used in the present invention will contain preferably from about 18.4% to about 27.6%, more preferably from about 20.7% to about 25.3%, most preferably about 23%, by weight of total phenolic antioxidants ("TPA").

The supercritical carbon dioxide extract of oregano used in the present invention will contain preferably from about 0.64% to about 0.96%, more preferably from about 0.72% to about 0.88%, most preferably about 0.8%, by weight of TPA.

The hydroalcoholic extract of turmeric used in the present invention will contain preferably from about 5.6% to about 8.4%, more preferably from about 6.3% to about 7.7%, most preferably about 7%, by weight of curcumin.

The hydroalcoholic extract of rosemary used in the present invention will contain preferably from about 18.4% to about 27.6%, more preferably from about 20.7% to about 25.3%, most preferably about 23%, by weight of TPA.

The hydroalcoholic extract of holy basil used in the present invention will contain preferably from about 1.6% to about 2.4%, more preferably from about 1.8% to about 2.2%, most preferably about 2%, by weight of ursolic acid.

The hydroalcoholic extract of green tea used in the present invention will contain preferably from about 36% to about 54%, more preferably from about 40.5% to about 49.5%, most preferably about 45%, by weight of polyphonies.

The hydroalcoholic extract of huzhang used in the present invention will contain preferably from about 6.4% to about 9.6%, more preferably from about 7.2% to about 8.8%, most preferably about 8%, by weight of resveratrol.

The hydroalcoholic extract of Chinese goldthread used in the present invention will contain preferably from about 4.8% to about 7.2%, more preferably from about 5.4% to about 6.6%, most preferably about 6%, by weight of berberine.

The hydroalcoholic extract of barberry used in the present invention will contain preferably from about 4.8% to about 7.2%, more preferably from about 5.4% to about 6.6%, most preferably about 6%, by weight of berberine.

In preferred embodiments, the composition of this invention further contains a pharmaceutically acceptable carrier. As used herein, the term "pharmaceutically acceptable carrier" is meant to include one or more pharmaceutically suitable, inactive excipients, carriers, diluents, adjuvants, and lubricants. Non-limiting examples of inactive excipients, carriers, diluents, lubricants, and adjuvants which can be used in the composition of the present invention include: cellulose, substituted cellulose, calcium carbonate, dicalcium phosphate, starches, lactose, modified food starches, dextrose, calcium sulfate, magnesium carbonate, magnesium stearate, stearic acid, glycerin, vegetable oils, polysorbates, lecithin, silicium dioxide, food glaze, talc, croscarmeilose sodium, povidone, water and gelatin. Additional inactive excipients, carriers, diluents, lubricants and adjuvants which may be used with the active-ingredient composition of this invention are disclosed in the Handbook of Food Additives (CRC Press), which is incorporated by reference herein in relevant part.

The pharmaceutically acceptable carrier can be present in any conventional amount used in an orally or topically administered compositions.

The present invention also provides a method for reducing inflammation in animals, preferably humans, suffering from inflammation. The method of this invention involves the steps of: (1) providing the composition of this invention; and (2) orally or topically administering the composition to the animal in an amount and for a time period effective to reduce inflammation in the animal.

The herbal composition of this invention can be administered orally or topically (including ophtamically, vaginally, rectally, intranasally, and the like).

The orally administered composition of this invention can be in any conventional form including, e.g., capsules (hard or soft), tablets, elixirs, powders, granules, suspensions in water or non-aqueous media, sachets, etc. Most preferably, the composition is in the form of one or more tablets, pills or capsules.

If in tablet, pill or capsule form, the composition of this invention is preferably orally ingested with a liquid, preferably water, more preferably with about 8 ounces of water.

Formulations for topical administration may include but are not limited to lotions, ointments, gels, creams, suppositories, drops, liquids, sprays, and powders. Conventional pharmaceutical carriers; aqueous, powder or oily bases; thickeners and the like may be necessary or desirable. Most preferably, the topically administered embodiment of the composition of this invention is in the form of a cream.

Preferably, the active-ingredient portion of the composition (i.e., the extracts) is orally administered in a daily dosage of at least about 500 mg, more preferably from about 700 mg to about 1000 mg, most preferably about 780 mg. In other words, the daily dosage of the composition of this invention will contain preferably at least about 500 mg, more preferably from about 700 mg to about 1000 mg, most preferably about 780 mg, of the herbal extracts. Inactive ingredients can be present in the composition in amounts conventionally used in orally ingested dietary supplements.

If consumed on a daily basis, the composition of this invention is preferably orally administered for a period of at least about 4 weeks. If the composition is not taken on a daily basis, the effective period of time for reducing inflammation will take longer and will depend on the frequency of consumption and the amount consumed.

Set forth in the Table below is a preferred embodiment of the orally administered composition (excluding inactive ingredients) of this invention. The amounts recited in the Table represent the preferred daily dosage (and one serving) of the ingredients listed.

TABLE

| Herb | Type Of Extract | Plant Part | Amount (mg) |
| --- | --- | --- | --- |
| Rosemary | supercritical $CO_2$ | leaf | 100 |
| Rosemary | hydroalcoholic (23% TPA - 34.5 mg) | leaf | 50 |
| Turmeric | supercritical $CO_2$ (45% turmerones - 4.5 mg) | rhizome | 10 |
| Turmeric | hydroalcoholic (7% curcumin - 7 mg) | rhizome | 100 |
| Ginger | supercritical $CO_2$ (30% pungent compounds - 16.2 mg 8% zingiberene - 4.3 mg) | rhizome | 54 |
| Ginger | post-supercritical $CO_2$ hydroalcoholic (3% pungent compounds - 1.4 mg) | rhizome | 46 |
| Holy basil | hydroalcoholic (2% ursolic acid - 2 mg) | leaf | 100 |
| Green tea | hydroalcoholic (45% polyphenols - 45 mg) | leaf | 100 |
| Huzhang | hydroalcoholic (8% resveratrol - 6.4 mg) | root & rhizome | 80 |
| Chinese Goldthread | hydroalcoholic (6% berberine - 2.4 mg) | root | 40 |
| Barberry | hydroalcoholic (6% berberine - 2.4 mg) | root | 40 |
| Oregano | supercritical $CO_2$ (0.8% TPA - 0.32 mg) | leaf | 40 |
| Scutellariae Baicalensis | hydroalcoholic (5:1) | root | 20 |

Preferably, the composition set forth in the Table above will also include extra virgin olive oil and yellow beeswax In preferred embodiments of the soft gel capsule form of the present invention, the capsule is composed of gelatin, vegetable glycerin, purified water and carob.

For oral administration of the above-recited formulation, the two soft gel capsules (together constituting one serving) are preferably taken daily, with 8 ounces of water.

What is claimed is:

1. An orally or topically administered herbal composition for reducing inflammation in an animal, suffering from inflammation, comprising: a therapeutically effective amount of a post-supercritical carbon dioxide alcoholic extract of ginger, therapeutically effective amounts of supercritical carbon dioxide extracts of rosemary, turmeric, oregano and ginger; and therapeutically effective amounts of hydroalcoholic extracts of holy basil, turmeric, scutellariae baicalensis, rosemary, green tea, huzhang, Chinese goldthread, and barberry.

2. A composition according to claim 1, wherein the composition is an orally administered composition.

3. A composition according to claim 2, wherein the composition is in the form of one or more capsules, one or more tablets, or one or more pills.

4. A composition according to claim 2, comprising:

(A) from about 4.5% to about 7.5% by weight of the post-supercritical carbon dioxide alcoholic extract of ginger;

(B) from about 5.5% to about 8.5% by weight of the supercritical carbon dioxide extract of ginger;

(C) from about 1.0% to about 1.5% by weight of the supercritical carbon dioxide extract of turmeric;

(D) from about 10.0% to about 16.0% by weight of the supercritical carbon dioxide extract of rosemary;

(E) from about 4.0% to about 6.0% by weight of the supercritical carbon dioxide extract of oregano;

(F) from about 10.0% to about 16.0% by weight of the hydroalcoholic extract of turmeric;

(G) from about 5.5% to about 8.0% by weight of the hydroalcoholic extract of rosemary;

(H) from about 10.0% to about 16.0% by weight of the hydroalcoholic extract of holy basil;

(I) from about 10.0% to about 16.0% by weight of the hydroalcoholic extract of green tea;

(J) from about 8.0% to about 12.0% by weight of the hydroalcoholic extract of huzhang;

(K) from about 4.0% to about 6.0% by weight of the hydroalcoholic extract of Chinese goldthread;

(L) from about 4.0% to about 6.0% by weight of the hydroalcoholic extract of barberry; and (M) from about 2.0% to about 3.0% by weight of the hydroalcoholic extract of scutellariae baicalensis.

5. A composition according to claim 2, comprising:
(A) from about 5.5% to about 6.5% by weight of the post-supercritical carbon dioxide alcoholic extract of ginger;
(B) from about 6% to about 8% by weight of the supercritical carbon dioxide extract of ginger;
(C) from about 1.2% to about 1.4% by weight of the supercritical carbon dioxide extract of turmeric;
(D) from about 11.5% to about 14.5% by weight of the supercritical carbon dioxide extract of rosemary;
(E) from about 4.5% to about 5.5% by weight of the supercritical carbon dioxide extract of oregano;
(F) from about 11.5% to about 14.5% by weight of the hydroalcoholic extract of turmeric;
(G) from about 6.0% to about 7.0% by weight of the hydroalcoholic extract of rosemary;
(H) from about 11.5% to about 14.5% by weight of the hydroalcoholic extract of holy basil;
(I) from about 11.5% to about 14.5% by weight of the hydroalcoholic extract of green tea;
(J) from about 9.0% to about 11.0% by weight of the hydroalcoholic extract of huzhang;
(K) from about 4.5% to about 5.5% by weight of the hydroalcoholic extract of Chinese goldthread;
(L) from about 4.5% to about 5.5% by weight of the hydroalcoholic extract of barberry; and
(M) from about 2.25% to about 2.75% by weight of the hydroalcoholic extract of scutellariae baicalensis.

6. A composition according to claim 2, wherein the composition comprises the supercritical carbon dioxide extract of ginger and the post-supercritical carbon dioxide hydroalcoholic extract of ginger at a weight ratio of from about 0.9 to about 1.4 parts of supercritical carbon dioxide extract per 1 part of post-supercritical carbon dioxide hydroalcoholic extract.

7. A composition according to claim 2, wherein the composition comprises the hydroalcoholic extract of turmeric and the supercritical carbon dioxide extract of turmeric at a weight ratio of from about 8 to about 12 parts of hydroalcoholic extract per 1 part of supercritical carbon dioxide extract.

8. A composition according to claim 2, wherein the composition comprises the supercritical carbon dioxide extract of rosemary and the hydroalcoholic extract of rosemary at a weight ratio of from about 1.6 to about 2.4 parts of supercritical carbon dioxide extract per 1 part of hydroalcoholic extract.

9. A composition according to claim 2, wherein the post-supercritical carbon dioxide hydroalcoholic extract of ginger comprises from about 2.4% to about 3.6% by weight of pungent compounds.

10. A composition according to claim 2, wherein the supercritical carbon dioxide extract of ginger comprises from about 24% to about 36% by weight of pungent compounds and from about 6.4% to about 9.6% by weight of zingiberene.

11. A composition according to claim 2, wherein the supercritical carbon dioxide extract of turmeric comprises from about 36% to about 54% by weight of turmerones.

12. A composition according to claim 2, wherein the supercritical carbon dioxide extract of rosemary comprises from about 18.4% to about 27.6% by weight of total phenolic antioxidants.

13. A composition according to claim 2, wherein the supercritical carbon dioxide extract of oregano comprises from about 0.64% to about 0.96% by weight of total phenolic antioxidants.

14. A composition according to claim 2, wherein the hydroalcoholic extract of turmeric comprises from about 5.6% to about 8.4% by weight of curcumin.

15. A composition according to claim 2, wherein the hydroalcoholic extract of rosemary comprises from about 18.4% to about 27.6% by weight of total phenolic antioxidants.

16. A composition according to claim 2, wherein the hydroalcoholic extract of holy basil comprises from about 1.6% to about 2.4% by weight of ursolic acid.

17. A composition according to claim 2, wherein the hydroalcoholic extract of green tea comprises from about 36% to about 54% by weight of polyphonies.

18. A composition according to claim 2, wherein the hydroalcoholic extract of huzhang comprises from about 6.4% to about 9.6% by weight of resveratrol.

19. A composition according to claim 2, wherein the hydroalcoholic extract of Chinese goldthread comprises from about 4.8% to about 7.2% by weight of berberine.

20. A composition according to claim 2, wherein the hydroalcoholic extract of barberry comprises from about 4.8% to about 7.2% by weight of berberine.

21. A composition according to claim 2, comprising:
(A) from about 4.5% to about 7.5% by weight of the post-supercritical carbon dioxide alcoholic extract of ginger, wherein the extract comprises from about 2.4% to about 3.6% by weight of pungent compounds;
(B) from about 5.5% to about 8.5% by weight of the supercritical carbon dioxide extract of ginger, wherein the extract comprises from about 24% to about 36% by weight of pungent compounds and from about 6.4% to about 9.6% by weight of zingiberene;
(C) from about 1.0% to about 1.5% by weight of the supercritical carbon dioxide extract of turmeric, wherein the extract comprises from about 36% to about 54% by weight of turmerones;
(D) from about 10.0% to about 16.0% by weight of the supercritical carbon dioxide extract of rosemary, wherein the extract comprises from about 18.4% to about 27.6% by weight of total phenolic antioxidants;
(E) from about 4.0% to about 6.0% by weight of the supercritical carbon dioxide extract of oregano, wherein the extract comprises from about 0.64% to about 0.96% by weight of total phenolic antioxidants;
(F) from about 10.0% to about 16.0% by weight of the hydroalcoholic extract of turmeric, wherein the extract comprises from about 5.6% to about 8.4% by weight of curcumin;
(G) from about 5.5% to about 8.0% by weight of the hydroalcoholic extract of rosemary, wherein the extract comprises from about 18.4% to about 27.6% by weight of total phenolic antioxidants;
(H) from about 10.0% to about 16.0% by weight of the hydroalcoholic extract of holy basil, wherein the extract comprises from about 1.6% to about 2.4% by weight of ursolic acid;
(I) from about 10.0% to about 16.0% by weight of the hydroalcoholic extract of green tea, wherein the extract comprises from about 36% to about 54% by weight of polyphenols;
(J) from about 8.0% to about 12.0% by weight of the hydroalcoholic extract of huzhang, wherein the extract comprises from about 6.4% to about 9.6% by weight of resveratrol;

(K) from about 4.0% to about 6.0% by weight of the hydroalcoholic extract of Chinese goldthread, wherein the extract from about 4.8% to about 7.2% by weight of berberine;

(L) from about 4.0% to about 6.0% by weight of the hydroalcoholic extract of barberry, wherein the extract from about 4.8% to about 7.2% by weight of berberine; and (M) from about 2.0% to about 3.0% by weight of the hydroalcoholic extract of scutellariae baicalensis;

further the composition comprises: (i) the supercritical carbon dioxide extract of ginger and the post-supercritical carbon dioxide hydroalcoholic extract of ginger at a weight ratio of from about 0.9 to about 1.4 parts of supercritical carbon dioxide extract per 1 part of post-supercritical carbon dioxide hydroalcoholic extract; (ii) the hydoalcoholic extract of turmeric and the supercritical carbon dioxide extract of turmeric at a weight ratio of from about 8 to about 12 parts of hydroalcoholic extract per 1 part of supercritical carbon dioxide extract; and (iii) the supercritical carbon dioxide extract of rosemary and the hydroalcoholic extract of rosemary at a weight ratio of from about 1.6 to about 2.4 parts of supercritical carbon dioxide extract per 1 part of hydroalcoholic extract.

22. A method for reducing inflammation in an animal suffering from inflammation, comprising the steps of:
(1) providing the composition of claim 1; and
(2) orally or topically administering the composition to the animal in an amount and for a time period sufficient to reduce the inflammation.

23. A method according to claim 22, wherein the composition provided in step (1) is in an orally administered form, and step (2) comprises orally administering the composition to a human.

24. A method according to claim 23, wherein the orally administered composition provided in step (1) is in the form of one or more capsules, one or more tablets, or one or more pills.

25. A method according to claim 23, wherein the orally administered composition provided in step (1) comprises:
(A) from about 4.5% to about 7.5% by weight of the post-supercritical carbon dioxide alcoholic extract of ginger;
(B) from about 5.5% to about 8.5% by weight of the supercritical carbon dioxide extract of ginger;
(C) from about 1.0% to about 1.5% by weight of the supercritical carbon dioxide extract of turmeric;
(D) from about 10.0% to about 16.0% by weight of the supercritical carbon dioxide extract of rosemary;
(E) from about 4.0% to about 6.0% by weight of the supercritical carbon dioxide extract of oregano;
(F) from about 10.0% to about 16.0% by weight of the hydroalcoholic extract of turmeric;
(G) from about 5.5% to about 8.0% by weight of the hydroalcoholic extract of rosemary;
(H) from about 10.0% to about 16.0% by weight of the hydroalcoholic extract of holy basil;
(I) from about 10.0% to about 16.0% by weight of the hydroalcoholic extract of green tea;
(J) from about 8.0% to about 12.0% by weight of the hydroalcoholic extract of huzhang;
(K) from about 4.0% to about 6.0% by weight of the hydroalcoholic extract of Chinese goldthread;

(L) from about 4.0% to about 6.0% by weight of the hydroalcoholic extract of barberry; and
(M) from about 2.0% to about 3.0% by weight of the hydroalcoholic extract of scutellariae baicalensis.

26. A method according to claim 23, wherein the composition provided in step (1) comprises the supercritical carbon dioxide extract of ginger and the post-supercritical carbon dioxide hydroalcoholic extract of ginger at a weight ratio of from about 0.9 to about 1.4 parts of supercritical carbon dioxide extract per 1 part of post-supercritical carbon dioxide hydroalcoholic extract.

27. A method according to claim 23, wherein the composition provided in step (1) comprises the hydroalcoholic extract of turmeric and the supercritical carbon dioxide extract of turmeric at a weight ratio of from about 8 to about 12 parts of hydroalcoholic extract per 1 part of supercritical carbon dioxide extract.

28. A method according to claim 23, wherein the composition provided in step (1) comprises the supercritical carbon dioxide extract of rosemary and the hydroalcoholic extract of rosemary at a weight ratio of from about 1.6 to about 2.4 parts of supercritical carbon dioxide extract per 1 part of hydroalcoholic extract.

29. A method according to claim 23, wherein, in the composition provided in step (1), the post-supercritical carbon dioxide hydroalcoholic extract of ginger comprises from about 2.4% to about 3.6% by weight of pungent compounds.

30. A method according to claim 23, wherein, in the composition provided in step (1), the supercritical carbon dioxide extract of ginger comprises from about 24% to about 36% by weight of pungent compounds and from about 6.4% to about 9.6% by weight of zingiberene.

31. A method according to claim 23, wherein, in the composition provided in step (1), the supercritical carbon dioxide extract of turmeric comprises from about 36% to about 54% by weight of turmerones.

32. A method according to claim 23, wherein, in the composition provided in step (1), the supercritical carbon dioxide extract of rosemary comprises from about 18.4% to about 27.6% by weight of total phenolic antioxidants.

33. A method according to claim 23, wherein, in the composition provided in step (1), the supercritical carbon dioxide extract of oregano comprises from about 0.64% to about 0.96% by weight of total phenolic antioxidants.

34. A method according to claim 23, wherein, in the composition provided in step (1), the hydroalcoholic extract of turmeric comprises from about 5.6% to about 8.4% by weight of curcumin.

35. A method according to claim 23, wherein, in the composition provided in step (1), the hydroalcoholic extract of rosemary comprises from about 18.4% to about 27.6% by weight of total phenolic antioxidants.

36. A method according to claim 23, wherein, in the composition provided in step (1), the hydroalcoholic extract of holy basil comprises from about 1.6% to about 2.4% by weight of ursolic acid.

37. A method according to claim 23, wherein, in the composition provided in step (1), the hydroalcoholic extract of green tea comprises from about 36% to about 54% by weight of polyphenols.

38. A method according to claim 23, wherein, in the composition provided in step (1), the hydroalcoholic extract of huzhang comprises from about 6.4% to about 9.6% by weight of resveratrol.

39. A method according to claim 23, wherein, in the composition provided in step (1), the hydroalcoholic extract of Chinese goldthread comprises from about 4.8% to about 7.2% by weight of berberine.

40. A method according to claim 23, wherein, in the composition provided in step (1), the hydroalcoholic extract of barberry comprises from about 4.8% to about 7.2% by weight of berberine.

41. A method according to claim 23, wherein the composition provided in step (1) comprises:

(A) from about 4.5% to about 7.5% by weight of the post-supercritical carbon dioxide alcoholic extract of ginger, wherein the extract comprises from about 2.4% to about 3.6% by weight of pungent compounds;

(B) from about 5.5% to about 8.5% by weight of the supercritical carbon dioxide extract of ginger, wherein the extract comprises from about 24% to about 36% by weight of pungent compounds and from about 6.4% to about 9.6% by weight of zingiberene;

(C) from about 1.0% to about 1.5% by weight of the supercritical carbon dioxide extract of turmeric, wherein the extract comprises from about 36% to about 54% by weight of turmerones;

(D) from about 10.0% to about 16.0% by weight of the supercritical carbon dioxide extract of rosemary, wherein the extract comprises from about 18.4% to about 27.6% by weight of total phenolic antioxidants;

(E) from about 4.0% to about 6.0% by weight of the supercritical carbon dioxide extract of oregano, wherein the extract comprises from about 0.64% to about 0.96% by weight of total phenolic antioxidants;

(F) from about 10.0% to about 16.0% by weight of the hydroalcoholic extract of turmeric, wherein the extract comprises from about 5.6% to about 8.4% by weight of curcumin;

(G) from about 5.5% to about 8.0% by weight of the hydroalcoholic extract of rosemary, wherein the extract comprises from about 18.4% to about 27.6% by weight of total phenolic antioxidants;

(H) from about 10.0% to about 16.0% by weight of the hydroalcoholic extract of holy basil, wherein the extract comprises from about 1.6% to about 2.4% by weight of ursolic acid;

(I) from about 10.0% to about 16.0% by weight of the hydroalcoholic extract of green tea, wherein the extract comprises from about 36% to about 54% by weight of polyphenols;

(J) from about 8.0% to about 12.0% by weight of the hydroalcoholic extract of huzhang, wherein the extract comprises from about 6.4% to about 9.6% by weight of resveratrol;

(K) from about 4.0% to about 6.0% by weight of the hydroalcoholic extract of Chinese goldthread, wherein the extract from about 4.8% to about 7.2% by weight of berberine;

(L) from about 4.0% to about 6.0% by weight of the hydroalcoholic extract of barberry, wherein the extract from about 4.8% to about 7.2% by weight of berberine; and (M) from about 2.0% to about 3.0% by weight of the hydroalcoholic extract of scutellariae baicalensis;

further the composition comprises: (i) the supercritical carbon dioxide extract of ginger and the post-supercritical carbon dioxide hydroalcoholic extract of ginger at a weight ratio of from about 0.9 to about 1.4 parts of supercritical carbon dioxide extract per 1 part of post-supercritical carbon dioxide hydroalcoholic extract; (ii) the hydroalcoholic extract of turmeric and the supercritical carbon dioxide extract of turmeric at a weight ratio of from about 8 to about 12 parts of hydroalcoholic extract per 1 part of supercritical carbon dioxide extract; and (iii) the supercritical carbon dioxide extract of rosemary and the hydroalcoholic extract of rosemary at a weight ratio of from about 1.6 to about 2.4 parts of supercritical carbon dioxide extract per 1 part of hydroalcoholic extract.

42. A method according to claim 23, wherein step (2) comprises orally administering the composition in a daily dosage of at least about 700 mg.

43. A method according to claim 23, wherein step (2) comprises orally administering the composition on a daily basis for at least 4 weeks.

\* \* \* \* \*